United States Patent [19]

Tanaka et al.

[11] Patent Number: 5,169,977

[45] Date of Patent: Dec. 8, 1992

[54] PROCESS FOR PURIFYING DIMETHYL-2,6-NAPHTHALENE DICARBOXYLATE

[75] Inventors: Toru Tanaka; Masami Matsumoto; Atsushi Ozaki; Hideaki Fujita, all of Okayama, Japan

[73] Assignee: Mitsubishi Gas Chemical Company, Inc., Tokyo, Japan

[21] Appl. No.: 669,247

[22] Filed: Mar. 14, 1991

[30] Foreign Application Priority Data

Mar. 15, 1990 [JP] Japan .................................. 2-62750
Mar. 16, 1990 [JP] Japan .................................. 2-64041

[51] Int. Cl.$^5$ ............................................ C07C 67/48
[52] U.S. Cl. .................................. 560/78; 562/486; 562/487
[58] Field of Search ................ 560/78; 562/486, 487

[56] References Cited

U.S. PATENT DOCUMENTS

| | | | |
|---|---|---|---|
| 3,517,053 | 6/1970 | Antonsen | 560/78 |
| 4,048,021 | 9/1977 | Takamoto et al. | 203/91 |
| 4,886,901 | 12/1989 | Holzhauer et al. | 560/77 |

FOREIGN PATENT DOCUMENTS

| | | |
|---|---|---|
| 0128586 | 11/1977 | German Democratic Rep. . |
| 46-003057 | 4/1971 | Japan . |
| 50-116461 | 9/1975 | Japan . |
| 1-249746 | 10/1989 | Japan . |

OTHER PUBLICATIONS

*Chemical Abstracts*, vol. 112, No. 11, Mar. 2, 1990, Columbus, Ohio USA, 98237m.

*Primary Examiner*—José G. Dees
*Assistant Examiner*—Vera C. Clarke
*Attorney, Agent, or Firm*—Browdy and Neimark

[57] ABSTRACT

A process for purifying crude 2,6-naphthalene dimethyl dicarboxylate (hereinunder referred to as 2,6-NDM) which comprises dissolving the crude 2,6-NDM into a $C_6$-$C_9$ aromatic hydrocarbon, then contacting the solution of 2,6-NDM and the hydrocarbon with an hydrotalcite-like laminar crystalline compound and activated carbon, then carrying out thermal filtration of the solution, and then cooling the solution to separate 2,6-NDM crystal from the solution is disclosed.

12 Claims, 1 Drawing Sheet

PROCESS FOR PURIFYING DIMETHYL-2,6-NAPHTHALENE DICARBOXYLATE

BACKGROUND OF THE INVENTION

This invention relates to a process for producing dimethyl-2,6-naphthalene dicarboxylate (hereinunder referred to as 2,6-NDM) which is useful as a raw material for high quality polyester.

In the prior art, 2,6-naphthalene dicarboxylic acid (hereinafter referred to as 2,6-NDA) has been produced by the following methods:

(1) Processes for producing 2,6-NDA which comprise oxidizing 2,6-dimethyl naphthalene in the presence of a catalyst comprising a heavy metal and a bromine compound are disclosed in U.S. Pat. No. 3,856,855 and Japanese Patent Publication (Kokai) No. 34153/1973.

(2) A process for producing 2,6-NDA which comprises oxidizing 2,6-diisopropyl naphthalene in the presence of a catalyst comprising Co and Mn is disclosed in Japanese Patent Publication (Kokai) No. 89445/1985.

(3) Processes for producing 2,6-NDA which comprise oxidizing a 2-alkyl-6-acyl naphthalene in the presence of a catalyst containing Co and Mn or Co, Mn and Br are disclosed in Japanese Patent Publication (Kokai) Nos. 61946/1987 and 67048/1987 and U.S. Pat. No. 4,764,638.

A naphthalene ring is more oxidizable than a benzene ring. So where a naphthalene compound is used as a reactant, many by-products and condensates are likely to be formed due to ring decomposition. Therefore, the 2,6-NDA produced by the above-mentioned methods contains large amount of impurities. Generally speaking, after the 2,6-NDA containing impurities is converted to 2,6-NDM, the 2,6-NDM is purified.

In the prior art, 2,6-NDM has been purified by (i) vacuum distillation; (ii) vacuum distillation and recrystallization [refer to Japanese Patent Publication (Kokai) No. 111055/1975, U.S. Pat. No. 4,048,021, Japanese Patent Publication (Kokai) No. 116461/1975 and Japanese Patent Publication (Kokoku) No. 35697/1982]; and (iii) recrystallization method by using a solvent, such as chlorobenzene, xylene or methanol [Japanese Patent Publication (Kokoku) Nos. 9697/1971 and 40349/1973].

It was thought that the vacuum distillation method is the easiest. However, since the melting point of 2,6-NDM is 190° C., it is difficult to carry out the distillation operation of 2,6-NDM early. That is, when 2,6-NDM is purified by the vacuum-distillation method, it is necessary to maintain the condenser at a temperature of more than 200°-210° C. in order to avoid solidification of 2,6-NDM in the condenser from occurring while the 2,6-NDM is being cooled in the condenser. When the distillation temperature is not so high when of purifying 2,6-NDM by vacuum distillation, the proportion of 2,6-NDM to be not condensed is increased. The 2,6-NDM which is not condensed in the condenser is condensed in a solidifying receiver which is maintained at a temperature less than the melting point of 2,6-NDM. When the proportion of 2,6-NDM to be condensed in the solidifying receiver becomes large, it becomes complicated to remove the 2,6-NDM from the solidifying receiver.

In addition, 2,6-NDM is likely to accumulate at the vacuum pump, etc. which results in the ability of the vacuum pump being lowered, so that the pipe is likely to become choked. It becomes necessary to raise the distillation temperature in order to avoid this trouble. However, when the distillation temperature rises, 2,6-NDM is likely to decompose or change in quality which results in a lowering in the quality of the product. In addition, highly viscous, high boiling point materials which are formed in the process adhere to the heat transfer surface of the heat exchanger. This is likely to lead to a decrease in heat transfer and cause local overheating.

As the 2,6-NDM distillate obtained by vacuum-distillation is not necessarily of a high quality, for example, in the invention of Japanese Patent Publication (Kokoku) No. 3057/1971 disclosing vacuum-distillation for purification of 2,6-NDM, an additive is added to the 2,6-NDM and distillation is effected to improve the acid value and color of 2,6-NDM.

2,6-NDM may be purified by recrystallization by using a solvent, such as chlorobenzene, etc. When the acid value and degree of coloration of crude 2,6-NDM are low, recrystallization by using the solvent can be easily carried out. However, when they are high, the recrystallization process must be repeated several times to purify the 2,6-NDM. The behavior of acidic materials and coloring materials is similar to that of 2,6-NDM, so 2,6-NDM cannot be completely purified by recrystallization. Therefore, in the case of purifying 2,6-NDM by recrystallization, an adsorbent is added to the 2,6-NDM during the recrystallizing operation, thereby removing the materials.

Japanese Patent Publication (Kokoku) No. 43731/1973 discloses a process for purifying 2,6-NDM which comprises adding an oxide or a hydroxide compound of an element belonging to Group I or II of the Periodic Table, an acid carbonate, a carbonate, an acid sulfate, an acid sulfite or an organic acid salt compound to crude 2,6-NDM to react with the acidic material contained in the 2,6-NDM, thereby depositing the salt in the solvent, and then carrying out thermal filtration to remove the salt. In this process, when the thermal filtration is not precisely carried out, the resulting 2,6-NDM is contaminated by a small amount of the additive and the salt which is dissolved in the solvent, and as a result, highly pure 2,6-NDM cannot be obtained.

SUMMARY OF THE INVENTION

The present inventors have researched methods for purifying crude 2,6-NDM which do not employ vacuum distillation. As a result, they have found that highly pure 2,6-NDM can be obtained by dissolving crude 2,6-NDM into an aromatic hydrocarbon having 6-9 carbon atoms and then allowing the impurities in the 2,6-NDM to be adsorbed onto a hydrotalcite-like laminar crystalline compound and activated carbon. This invention is based on this discovery.

This invention relates to a process for purifying crude 2,6-NDM which comprises:

a step of dissolving the crude 2,6-NDM into an aromatic hydrocarbon having 6-9 carbon atoms;

a step of contacting the solution containing the crude 2,6-NDM with a hydrotalcite-like laminar crystalline compound (hereinunder referred to as hydrotalcite compound) and activated carbon to allow the impurities in the 2,6-NDM to be adsorbed onto the compound and the activated carbon;

a step of carrying out thermal filtration of the solution; and a step of cooling the filtrate to obtain 2,6-NDM crystal.

Actually, a variety of purifying operations may be carried out depending on the properties of 2,6-NDM to be purified.

Operation (1)

When the level of impurities contained in crude 2,6-NDM is small, the following operation is carried out.

Crude 2,6-NDM is dissolved into an aromatic hydrocarbon having 6-9 carbon atoms. Then a hydrotalcite compound and the activated carbon are added to the solution, thereby allowing the impurities to be adsorbed onto the compound and the activated carbon. Then, thermal filtration is effected to recover pure 2,6-NDM. In this operation, it is preferable for thermal filtration of the solution containing the crude 2,6-NDM in the aromatic hydrocarbon to be carried out before adding to the solution a hydrotalcite compound and activated carbon to remove any materials which are insoluble in the aromatic hydrocarbon.

The resulting 2,6-NDM crystal is further purified in the following method: The 2,6-NDM crystal is dissolved into dioxane which was heated to the boiling point at an atmospheric pressure; and then thermal filtration is effected and the 2,6-NDM is recrystallized.

Operation (2)

When the level of impurities contained in crude 2,6-NDM is large, the following operation is carried out.

Crude 2,6-NDM is heated to 210°-260° C. at 300-800 mmHg to melt the 2,6-NDM. A preheated aromatic hydrocarbon having 6-9 carbon atoms is added to the melted crude 2,6-NDM and the 2,6-NDM is evaporated to remove high boiling point materials. Thereafter, the hydrotalcite compound and activated carbon are added to the resulting 2,6-NDM to allow the impurities in the 2,6-NDM to be adsorbed onto the hydrotalcite compound and the activated carbon. In this operation, in order to reduce the amount of the hydrotalcite compound employed, an alkaline compound including an alkali metal or an alkaline earth metal is added to the 2,6-NDM before adding the hydrotalcite compound to the 2,6-NDM.

The problems caused by vacuum distillation are avoided in the present invention. According to the present invention, 2,6-NDM with extremely high purity can be obtained as shown in the following working examples. Therefore, high quality polyethylene naphthalate (PEN) resin or film can be derived from the highly pure 2,6-NDM. Therefore, the present invention is significant from an industrial point of view.

DETAILED DESCRIPTION OF THE INVENTION

Figure 1:
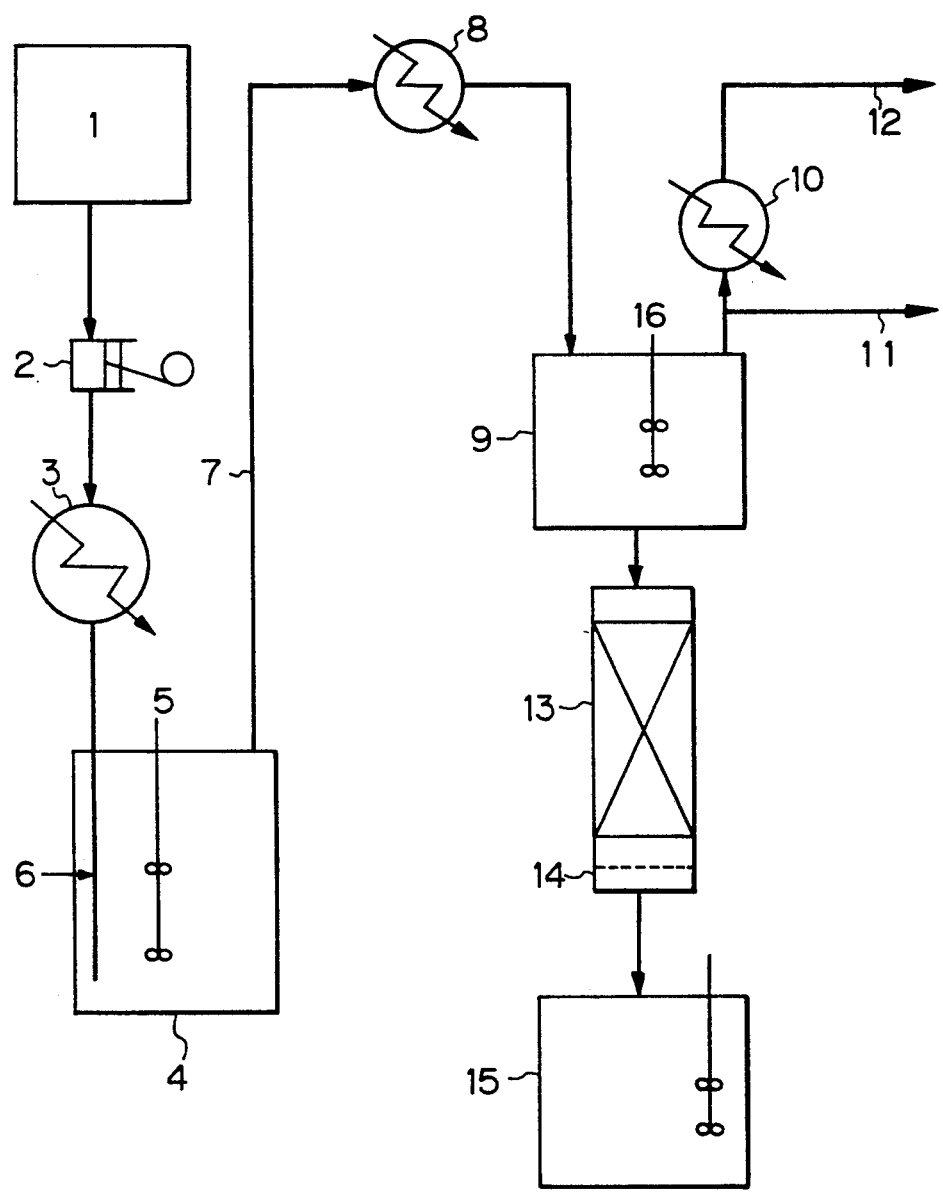
FIG. 1 is a flow sheet for carrying out the above-mentioned Operation (2).

In this invention, processes for producing crude 2,6-NDM are not critical. For example, 2,6-NDA is prepared by oxidizing a 2,6-dialkyl naphthalene or a 2-alkyl-6-acylnaphthalene in an acetic acid solvent in the presence of a catalyst comprising a heavy metal and bromine. 2,6-NDM is prepared by esterifying 2,6-NDA by well known methods.

(1) When the level of impurities in crude 2,6-NDM is small, that is, when the crude 2,6-NDM has an acid value of not more than 5 mg KOH/g and color index (b) of not more than 10, and preferably an acid value of 0.2-2 mg KOH/g and color index (b value) of not more than 5, the above-mentioned Operation (1) is effected.

Examples of the aromatic hydrocarbons having 6-9 carbon atoms include benzene, toluene, xylenes, pseudocumene, mesitylene, ethyl toluene and cumene. The amount of the hydrocarbon employed may be in the range of 4-14 times by weight of the crude 2,6-NDM.

Crude 2,6-NDM may be dissolved in the hydrocarbon at a temperature of 100°-140° C. When the temperature is less than 100° C., the amount of the absorbents employed must be increased, or the absorption time must be prolonged, because the adsorption of the impurities by absorbents is not sufficient. When the temperature is more than 140° C., it adds unnecessarily to the cost because the amount and speed of absorption are not much increased.

The thermal filtration of the solution in which the crude 2,6-NDM is dissolved may be carried out at the above-mentioned temperature to remove the insoluble impurities.

(2) When the amount of impurities in crude 2,6-NDM is large, that is, when crude 2,6-NDM has an acid value of not less than 5 mg KOH/g and a color index (b value) of not more than 10, the above-mentioned Operation (2) may be carried out.

Alkaline compounds may be used for reducing the amount of adsorbents employed. When the acid value is not less than 10, a large amount of acidic material is contained in the evaporated 2,6-NDM and the amount of the alkaline compound to be added to the evaporated 2,6-NDM becomes large. Therefore, the neutralized material is deposited on the evaporator. This causes choking of the heat exchanger and decrease in heat transfer. The alkaline compounds include alkaline compounds including an alkali metal belonging Group I of the Periodic Table or an alkaline earth metal belonging to Group II of the Periodic Table. Examples of the alkaline compounds include oxides, hydroxides, carbonates or acid carbonates of alkali metal or alkaline earth metal. It is preferable that the acid value of the crude 2,6-NDM is made zero by using an alkaline compound in an amount which is more than the equivalent of the acid value.

The pressure for allowing the crude 2,6-NDM to be evaporated may be in the range of 300-800 mmHg (absolute pressure). In this case, it is unnecessary to maintain a high degree of vacuum to evaporate the 2,6-NDM.

The evaporating operation may be carried out in the presence of a solvent, that is an aromatic hydrocarbon having 6-9 carbon atoms. When the evaporating operation is carried out at a very low pressure, a $C_9$ aromatic hydrocarbon is preferably used. When the evaporating operation is carried out at an atmospheric pressure, a xylene is preferably used.

The pressure for evaporating crude 2,6-NDM depends on the ratio of 2,6-NDM to the aromatic hydrocarbon, the evaporating temperature, the flow rate of the aromatic hydrocarbon to the evaporator and the temperature of the condenser.

If the evaporator is supplied with the theoretically necessary minimum amount of the aromatic hydrocarbon, the pressure in the evaporator may be approximated by the following equation:

$$\pi = p\left(1 + \frac{W_2}{W_1} \times \frac{244}{M_2}\right)$$

π: pressure (during evaporation) (mmHg abs)
p: saturated vapor pressure of 2,6-NDM (mmHg abs)
$W_1$: amount of 2,6-NDM evaporated (g/H)
$W_2$: amount of solvent evaporated (g/H)
$M_2$: molecular weight of solvent In order to allow a high concentration of 2,6-NDM to be evaporated, the evaporation is carried out at highly saturated vapor pressure and at high temperature, or by making the flow rate of the solvent as small as possible by using a solvent with a low molecular weight.

When the pressure (abs) is less than 300 mmHg, the cooling operation in the condenser is not sufficient; and as a result loss of the aromatic hydrocarbon becomes large. When the pressure (abs) is more than 800 mmHg, a high temperature is required for allowing 2,6-NDM to be evaporated, and this causes a lowering in the quality of the resulting 2,6-NDM.

The temperature which enables 2,6-NDM to be evaporated is in the range of 210°–270° C., and preferably 220°–260° C. When the temperature is less than 210° C., the 2,6-NDM content in the mixed gas becomes low because the vapor pressure of 2,6-NDM is low. When the temperature is more than 270° C., a change in properties of 2,6-NDM is caused, and as a result, the properties of the product are degraded.

It is preferable to blow the heated aromatic hydrocarbon vapor in an amount of as much as possible into melted 2,6-NDM, 2,6-NDM is likely to be solidified at the portion around the blowing pipe and as a result, the solidified 2,6-NDM may choke the pipe, so it is preferable to feed into 2,6-NDM the hydrocarbon with a temperature of 180°–260° C.

The type of the evaporator and the shape of the evaporator are not critical. However, an internal heat transfer pipe for evaporating 2,6-NDM or an external heating means therefor, a gas feeding pipe for blowing an aromatic hydrocarbon gas into 2,6-NDM, agitating means for allowing the hydrocarbon gas to be dispersed into 2,6-NDM and promoting the evaporation of 2,6-NDM, and an exit pipe for withdrawing the mixed gas of evaporated 2,6-NDM and the aromatic hydrocarbon are required in the evaporator.

It is preferable to feed the aromatic hydrocarbon gas into a liquid phase of 2,6-NDM in order to promote the evaporation of 2,6-NDM. However, part of the hydrocarbon gas is fed to the gaseous phase of the evaporator in order to avoid the entrainment of the 2,6-NDM mist. The evaporating operation may be continuous or batchwise.

A usual condenser is used for condensing the evaporated gas. It is preferable to maintain the condensation temperature as high as possible in order to prevent deposit of 2,6-NDM. The 2,6-NDM and the aromatic hydrocarbon are introduced into a receiver through the condenser. The non-condensed solvent from the receiver may be condensed in the second condenser in order to reflux into the receiver, or the part of the solvent which is condensed in the second condenser and withdrawn outside.

The 2,6-NDM solution recovered in the receiver is heated in order to solve the crystallized 2,6-NDM.

(3) The solution of crude 2,6-NDM in the aromatic hydrocarbon having 6–9 carbon atoms contacts solid adsorbents to remove a small amount of impurities. The solid adsorbents comprise the hydrotalcite compound and activated carbon. The hydrotalcite compound is one of inorganic anion exchangers and is represented by $Mg_6Al_2(OH)_{16}CO_34H_2O$ or $Mg_{4.5}Al_2(OH)_{13}CO_33.5\text{-}H_2O$. For example, the hydrotalcite compound which is sold by Kyowa Chemical Industry Co., Ltd. under the trade names of KW 500s Series and KW 1000 Series may be used. The compound formed of finely divided particles having an apparent gravity of 3.4–3.8 g/ml and a BET specific surface area of 100–600 $m^3/g$ is preferable.

Activated carbon is used for removing colored materials. Granules or powder activated carbon made from coconut shell is preferable.

The amount of adsorbents employed depends on the nature of crude 2,6-NDM. Usually, the hydrotalcite compound and activated carbon may be used in an amount of 3–10% by weight each on the basis of weight of 2,6-NDM.

The adsorbing operation may be a batch process comprising adding a suitable amount of adsorbents to 2,6-NDM, leaving the mixture to stand for a definite time and next separating the absorbents from the solution by precision filtration. Alternatively, the operation may be a continuous process comprising passing the 2,6-NDM solution through a stationary adsorbent layer at LSV of about 1 $hour^{-1}$.

After the impurities in the 2,6-NDM are adsorbed onto the adsorbents, the 2,6-NDM solution is heat-filtered to obtain a clear purified 2,6-NDM solution. Any filters under pressure having heating means may be used as a filter. Leaf-like filter under pressure and horizontal type filter under pressure can be used. Funda filter under pressure is preferable.

The adsorption temperature depends on the concentration of 2,6-NDM. When the concentration of 2,6-NDM is low, the adsorption can be effected at a temperature of less than the boiling point of the solvent. When the concentration of 2,6-NDM is high, an additional solvent is added to the system as occasion demands, and the adsorption is effected under pressure.

When filtration is effected, it is necessary to previously increase the filtering characteristics by using a filter auxiliary, such as diatomaceous earth. The filtrate obtained by thermal filtration is cooled in a container equipped with an agitator to crystallize 2,6-NDM.

The cooling temperature depends on the concentration of the 2,6-NDM solution. The cooling temperature may be usually about 20° C. The purified crystalline 2,6-NDM separated from the solution. The 2,6-NDM cake is reslurried in new solvent to remove the mother liquor adhered on the surface of crystal. If necessary, the crystal is dried.

(4) In the case of further purifying 2,6-NDM crystal, the crystal is redissolved in dioxane solvent. Then, activated carbon is added to the solution to remove impurities, and the activated carbon is removed by thermal filtration. The 2,6-NDM crystal can be obtained by recrystallization.

The temperature for dissolving the 2,6-NDM crystal in dioxane solvent is preferably the boiling point of dioxane at atmospheric pressure in order to save the amount of solvent. The amount of dioxane employed may be 5–15 times by weight of 2,6-NDM, and the activated carbon may be used as absorbent. The amount of the activated carbon employed may be 2–5% by weight on the basis of weight of purified 2,6-NDM. The adsorption time may be usually 1-2 hours. After the thermal filtration and the recrystallization are carried out, the crystallized 2,6-NDM is separated by well-known method and is dried.

(5) FIG. 1 is a flow sheet in case of Operation (2) (when crude 2,6-NDM contains a relatively large amount of impurities).

Crude 2,6-NDM and an alkaline compound including an alkali metal or an alkaline earth metal are charged into evaporator 4 equipped with internal heat exchanger (not shown), external heat exchanger (not shown) and agitator 5. The contents are melted by heating.

An aromatic hydrocarbon (solvent) is stored in tank 1. The solvent is fed by solvent-feeding pump 2, and is heated to 180°–260° C. by solvent heater 3. The solvent is fed into evaporator 4.

The solvent vapor is fed from nozzle 6 into the liquid phase and the gaseous phase of evaporator 4. The mixed gas of 2,6-NDM gas and the aromatic hydrocarbon gas enters into first receiver 9 through exhaust gas line 7 and first condenser 8. First receiver 9 is equipped with agitator 16 and heating apparatus (not shown). Non-condensed solvent gas is condensed in second condenser 10 and refluxed. Part of the condensed solvent is withdrawn from line 11 in order to adjust the concentration of condensing solution. Non-condensed gas is withdrawn from line 12. 2,6-NDM solution is fed from first receiver 9 to adsorption column 13. The lower part of column 13 is provided with filter 14. After the impurities in the 2,6-NDM solution are adsorbed in column 13, the solution is fed to second receiver 15. Thereafter the, 2,6-NDM solution in the receiver is cooled, and 2,6-NDM is crystallized, washed and dried.

EXAMPLE

The present invention is further explained by the following non-limiting examples. The acid value which is a measure of quality of the 2,6-NDM product was measured by titration.

Color index (L value), (a value) and (b value) of the product were obtained by measuring a sample plate obtained by compression-molding 2,6-NDM powder. The measurement was made by analyzing the values obtained by color difference meter. "L" value (brightness), "a" value [red (+)-green (−)] and "b" value [yellow (+)-blue (−)] were compared.

EXAMPLE 1

2-methyl-6-butyryl naphthalene was oxidized in the presence of a heavy metal and bromine to obtain crude 2,6-NDA. Into a titanium autoclave equipped with an agitator, a heating means and a reflux condenser were charged 100 g of the crude 2,6-NDA as prepared above, 900 g of methyl alcohol and 10 g of sulfuric acid. The autoclave, pressurized with nitrogen gas to 0.2 kg/cm$^2$G was closed, and, was heated to 130° C. The autoclave was cooled after 2.5 hours to obtain crude 2,6-NDM. The resulting crude 2,6-NDM had an acid value of 3.0 mg KOH/g and a color index ("L" value of 80.5, "a" value of 1.2 and "b" value of 8.9).

Thereafter, a thermal filter apparatus having a 500 ml autoclave with an agitator inside and a pressure filter of 200 mm outside diameter (Adbantic Toyo Co., Ltd., LS-90 V) at its bottom was prepared. Into the thermal filter apparatus were charged 80 g of the crude 2,6-NDM as prepared above and 400 g of xylene. The mixture was heated to the boiling point at atmosphere pressure. Thermal filtration was carried out by opening the valve connecting with the filter, thereby removing insoluble materials. The filtrate cake was charged again into the thermal filter apparatus, and then 4.0 g of hydrotalcite compound (Kyowa Chemical Industry Co., Ltd.; KW 500 SN) and 1.6 g of powdery activated carbon as adsorbents were added to the 2,6-NDM solution. The mixture was heated to the boiling point at atmospheric pressure, and the mixture was maintained at that temperature for 1 hour. The thermal filtration was carried out in the same way as above. The filtrate was cooled to 20° C. to crystallize 2,6-NDM. The 2,6-NDM crystal was filtered by a glass filter. The cake was dried. The 2,6-NDM had an acid value of 0.05 mg KOH/g and a color index ("L" value of 93.2, "a" value of 0.5 and "b" value of 3.9).

The resulting purified 2,6-NDM (60 g), dioxane (600 g) and activated carbon (1.8 g) were charged into the thermal filter apparatus as mentioned above. The mixture was heated to the boiling point at atmospheric pressure to allow the purified 2,6-NDM to be dissolved in the dioxane. The mixture was kept at that temperature for 1 hour. Thereafter, thermal filtration was carried out in the same way as above. The filtrate was cooled to 20° C. to crystallize the 2,6-NDM. The 2,6-NDM cake was filtered and dried. The resulting 2,6-NDM crystal had an acid value of 0.03 mg KOH/g and a color index ("L" value of 95.2, "a" value of −0.1 and "b" value of 2.3).

Control Run 1

Into the thermal filter apparatus of Example 1 were charged 80 g of crude 2,6-NDM obtained by Example 1 and 400 g of xylene. To the mixture were added 5.6 g of granular magnesium oxide and 1.6 g of powdery activated carbon without previously carrying out thermal filtration. The mixture was heated to the boiling point at an atmospheric pressure. The mixture was kept at that temperature for 2 hours. Thermal filtration was carried out in the same way as in Example 1. The resulting filtrate was cooled to 20° C. to obtain purified 2,6-NDM. The 2,6-NDM was dried. The resulting 2,6-NDM had an acid value of 1.3 mg KOH/g and a color index ("L" value of 89.9, "a" value of 0.8 and "b" value of 4.9).

The resulting purified 2,6-NDM (60 g), dioxane (600 g) and powderous activated carbon (1.8 g) were charged into the thermal filter apparatus as mentioned above. The mixture was heated to the boiling point at an atmospheric pressure to allow the purified 2,6-NDM to be dissolved in the dioxane. The mixture was kept at that temperature for 1 hour. Thereafter, thermal filtration was carried out in the same way as above. The filtrate was cooled to 20° C. to crystallize the 2,6-NDM crystal. The 2,6-NDM crystal was filtered and dried. The resulting 2,6-NDM crystal had an acid value of 0.55 mg KOH/g and a color index ("L" value of 93.4, "a" value of 0.2 and "b" value of 3.9).

EXAMPLE 2

Into the thermal filter apparatus of Example 1 were charged 60 g of the crude 2,6-NDM as prepared in Example 1 and 360 g of xylene. The mixture was heated to the boiling point at an atmospheric pressure. Thermal filtration was carried out in the same way as in Example 1, thereby removing insoluble materials. The filtrate was charged into the thermal filter apparatus, and then 4.0 g of hydrotalcite compound (Kyowa Chemical Industry Co., Ltd.; KW 1000) and 1.8 g of powdery activated carbon as adsorbents were added to the 2,6-NDM solution. The mixture was heated to the boiling point at atmospheric pressure, and the mixture was maintained at that temperature for 4 hours. The thermal filtration was carried out in the same way as above. The filtrate was cooled to 20° C. to crystallize 2,6-NDM. The 2,6-NDM crystal was filtered by a glass filter to obtain purified 2,6-NDM. The 2,6-NDM was dried. The 2,6-NDM had an acid value of 0.039 mg KOH/g and a color index ("L" value of 94.9, "a" value of 0.2 and "b" value of 3.2).

The resulting purified 2,6-NDM (45 g), dioxane (270 g) and powderous activated carbon (1.0 g) were charged into the thermal filter apparatus as mentioned above. The mixture was heated to the boiling point at an atmospheric pressure to allow the purified 2,6-NDM to be dissolved in the dioxane. The mixture was kept at that temperature for 1 hour. Thereafter, thermal filtration was carried out in the same way as above. The filtrate was cooled to 20° C. to crystallize the 2,6-NDM crystal. The 2,6-NDM crystal was filtered and dried. The resulting 2,6-NDM crystal had an acid value of 0.008 mg KOH/g and a color index ("L" value of 96.0, "a" value of −0.2 and "b" value of 1.9).

Control Run 2

Into the thermal filter apparatus of Example 1 were charged 80 g of crude 2,6-NDM obtained by Example 1 and 480 g of toluene. The mixture was heated to the boiling point at an atmospheric pressure. Thermal filtration was carried out in the same way as in Example 1 to remove insoluble materials. The filtrate was charged into the thermal filter apparatus again. To the mixture were added 6.4 g of synthetic magnesium silicate (Kyowa Chemical Industry Co., Ltd.; KW 700) as an acid adsorbent. The mixture was heated to the boiling point at an atmospheric pressure. The mixture was kept at that temperature for 2 hours. Thermal filtration was carried out in the same way as above. The resulting filtrate was cooled to 30° C. to obtain purified 2,6-NDM. The 2,6-NDM was dried. The resulting 2,6-NDM had an acid value of 0.3 mg KOH/g and a color index ("L" value of 82.5, "a" value of 1.0 and "b" value of 6.1).

The resulting dried purified 2,6-NDM (60 g), dioxane (600 g) and powdery coconut shell activated carbon (4.8 g) were charged into the thermal filter apparatus as mentioned above. The mixture was heated to the boiling point at an atmospheric pressure to allow the purified 2,6-NDM to be dissolved in the dioxane. The mixture was kept at that temperature for 3 hours. Thereafter, thermal filtration was carried out in the same way as above. The filtrate was cooled to 20° C. to deposit the 2,6-NDM crystal. The 2,6-NDM crystal was filtered and dried. The resulting 2,6-NDM crystal had an acid value of 0.16 mg KOH/g and a color index ("L" value of 89.9, "a" value of 0.4 and "b" value of 4.1).

EXAMPLE 3

2,6-NDM having an acid value of 6.5 mg KOH/g and a color index ("L" value of 84.4, "a" value of 1.6 and "b" value of 15.8) measured by color difference meter was synthesized. Into a 1-l evaporator equipped an agitator and a heating jacket were charged 500 g of the above 2,6-NDM. The evaporator was closed and purged with nitrogen gas. The evaporator was heated to 240° C., and the 2,6-NDM was melted and agitated. m-xylene was continuously charged by solvent-feeding pump at a rate of 1500 g/H into the gaseous phase and the liquid phase (ratio of 1:3) of the evaporator which was heated at 135° C. The 2,6-NDM was vaporized by the solvent vapor which was fed. The resulting mixed gas of the solvent vapor and the 2,6-NDM vapor was fed to a first condenser through an exhaust gas line which had previously been heated and insulated. The solution of 2,6-NDM in m-xylene was recovered in a first receiver. Non-condensed m-xylene was condensed in a second condenser to recirculate part of the resulting m-xylene to evaporator. Feeding of m-xylene was terminated when the temperature of the bottom of the evaporator amounted to 270° C. The concentration of 2,6-NDM was 8.5 wt % in the first receiver which was maintained at 135° C.

Into an adsorption column were charged 50 g of finely divided anion exchanger complex metal oxide particles having hydrotalcite structure (Kyowa Chemical Industry Co., Ltd.; Kyoward 500SN) and 50 g of particulate coconut shell activated carbon.

The two adsorbents were placed in a laminar state. The 2,6-NDM solution was passed through the adsorbent layer at LSV 1.0 hour$^{-1}$. A filter having a pore size of 2 μm average was placed at the bottom of the column. The 2,6-NDM solution was filtered by the filter. The filtrate was fed to the second receiver and was cooled to 30° C. to deposit 2,6-NDM crystal. The 2,6-NDM crystal was washed with m-xylene and methanol and dried to obtain purified 2,6-NDM. The resulting purified 2,6-NDM had an acid value of 0.05 mg KOH/g and a color index ("L" value of 95.9, "a" value of −1.2 and "b" value of −0.2). The color index was measured by color difference meter.

EXAMPLE 4

Into the evaporator of Example 3 were charged 500 g of the 2,6-NDM of Example 3 and 5 g of anhydrous sodium carbonate. The evaporator was closed and purged with nitrogen gas. The evaporator was heated to 240° C. to melt the 2,6-NDM. The melted 2,6-NDM was agitated. The evaporator was depressurized to 400 mmHg (abs) by reduced pump, and mesitylene which was heated at 140° C. was continuously charged by solvent-feeding pump at a rate of 1200 g/H into the gaseous phase and the liquid phase (ratio by weight of 1:8) of the evaporator which was maintained at 400 mmHg (abs). The mixed gas of 2,6-NDM and mesitylene which were vaporized were condensed in the first condenser, and recovered in the first receiver. Non-condensed mesitylene vapor etc. was condensed in the second condenser. Part of the condensed mesitylene was recirculated. Feeding of mesitylene was terminated when the temperature of the bottom of evaporator amounted to 270° C. The concentration of 2,6-NDM was 13.8 wt % in the first receiver which was maintained at 135° C.

Into an adsorption column were charged 50 g of finely divided anion exchanger complex metal oxide particles having hydrotalcite structure (Kyowa Chemical Industry Co., Ltd.; Kyoward 500SN) and 50 g of particulate coconut shell activated carbon.

The two adsorbents were placed in a laminar state. The 2,6-NDM solution was passed through the adsorbent layer at LSV 0.8 hour$^{-1}$. A filter having a pore size of 2 μm average was placed at the bottom of the column. The 2,6-NDM solution was filtered by the filter. The filtrate was fed to the second receiver and was cooled to 30° C. to deposit 2,6-NDM crystal. The 2,6-NDM crystal was washed with m-xylene and methanol and dried to obtain purified 2,6-NDM. The resulting purified 2,6-NDM had an acid value of 0.014 mg KOH/g and a color index ("L" value of 96.7, "a" value of −0.4 and "b" value of −0.4 as was measured by color difference meter). The freezing point thereof was 190.2° C.

Control Run 3

Into the evaporator of Example 3 were charged 500 g of the 2,6-NDM of Example 3. The evaporator was closed and purged with nitrogen gas. The evaporator was heated to 230° C. to melt the 2,6-NDM. The melted 2,6-NDM was agitated. The evaporator was depressurized to 400 mmHg (abs) by vacuum, and methanol which was heated at 230° C. was continuously charged at a rate of 1000 g/H into the gaseous phase and the liquid phase (ratio by weight of 1:5) of the evaporator which was maintained at 400 mmHg (abs). The mixed gas of 2,6-NDM and methanol which were vaporized were condensed in the first condenser, and recovered in the first receiver. Non-condensed methanol vapor etc. was condensed in the second condenser. Part of the condensed methanol was refluxed. Feeding of methanol was terminated when the temperature of the bottom of evaporator amounted to 270° C.

2,6-NDM in an amount of 9.5 wt % was present in a slurry state in the first receiver. After cooling the slurry, all of the slurry was withdrawn from the first receiver. Into a 5-l autoclave equipped with a heating means and an agitator was charged the above slurry. The autoclave was closed and pressurized to 2 kg/cm²G with nitrogen gas, and then the autoclave was heated to 120° C. and the contents was agitated. After 1 hour, the contents were cooled and the solid was separated from the liquid. The resulting crystal was washed with methanol and dried. The resulting 2,6-NDM had an acid value of 1.9 mg KOH/g and a color index ("L" value of 94.2, "a" value of 0.2 and "b" value of 3.2 as measured by color difference meter). The freezing point thereof was 190.0° C.

What is claimed is:

1. A process for purifying crude 2,6-naphthalene dimethyl dicarboxylate (hereinunder referred to as 2,6-NDM) which comprises:
    a step of dissolving the crude 2,6-NDM into an aromatic hydrocarbon having 6-9 carbon atoms;
    a step of contacting the solution in the crude 2,6-NDM in the hydrocarbon with a hydrotalcite compound and activated carbon to allow the impurities in the crude 2,6-NDM to be adsorbed onto the compound and the activated carbon;
    a step of carrying out thermal filtration of the solution; and
    a step of cooling the filtrate to obtain 2,6-NDM crystals.

2. The process of claim 1 wherein the aromatic hydrocarbon is selected from the group consisting of benzene, toluene, xylenes, pseudocumene, mesitylene, ethyl toluenes and cumene.

3. The process of claim 1 wherein the temperature for dissolving the crude 2,6-NDM into the hydrocarbon is in the range of 100°-140° C.

4. The process of claim 1 wherein the thermal filtration is carried out at a temperature of 100°-140° C.

5. The process of claim 1 wherein the process includes an additional step of dissolving the resulting 2,6-NDM crystal into dioxane which is being heated at a boiling point of dioxane at atmospheric pressure, followed by carrying out thermal filtration of the solution and recrystallizing 2,6-NDM.

6. A process for purifying crude 2,6-NDM which comprises:
    a step of adding a heated aromatic hydrocarbon having 6-9 carbon atoms to melted crude 2,6-NDM which is being heated at 210°-260° C. at 300-800 mmHg to evaporate the 2,6-NDM by the heat of the aromatic hydrocarbon;
    a step of condensing the resulting mixed gas of the 2,6-NDM and the aromatic hydrocarbon;
    a step of contacting the resulting condensed solution using a hydrotalcite compound at least one solid adsorbent to remove a small amount of impurities from the solution; and
    a step of cooling the resulting solution to separate 2,6-NDM crystals from the solution.

7. The process of claim 6 wherein the aromatic hydrocarbon is selected from the group consisting of benzene, toluene, xylenes, pseudocumene, mesitylene, ethyl toluenes and cumene.

8. The process of claim 6 wherein the process includes an additional step of adding an alkaline compound of an alkali metal or an alkaline earth metal to the solution of 2,6-NDM and the aromatic hydrocarbon before contacting the solution with the adsorbent.

9. The process of claim 8 wherein the alkaline compound is selected from the group consisting of oxides, hydroxides, carbonates, and acid carbonates of an alkali metal or alkaline earth metal.

10. The process of claim 6 wherein the pressure for evaporating the crude 2,6-NDM is expressed in the following equation:

$$\pi = p\left(1 + \frac{W_2}{W_1} \times \frac{244}{M_2}\right)$$

$\pi$: pressure (during evaporation) (mmHg abs)
p: saturated vapor pressure of 2,6-NDM (mmHg abs)
$W_1$: amount of 2,6-NDM evaporated (g/H)
$W_2$: amount of solvent evaporated (g/H)
$M_2$: molecular weight of solvent.

11. The process of claim 6 wherein the process includes an additional step of dissolving the resulting 2,6-NDM crystal into dioxane which is being heated at the boiling point of dioxane at an atmospheric pressure, followed by carrying out thermal filtration and recrystallizing 2,6-NDM.

12. The process of claim 6 wherein the adsorbent comprises said hydrotalcite compound in a laminar crystalline form and activated carbon.

* * * * *